United States Patent [19]

Hinnergardt et al.

[11] Patent Number: 5,902,616

[45] Date of Patent: May 11, 1999

[54] PROCESS FOR PREPARING A TOMATO SAUCE USING A PECTINASE ENZYME

[75] Inventors: Larry Charles Hinnergardt, Lodi, Calif.; Paul Szalkucki, Seymour; Mary Lou Sando, Naugatuck, both of Conn.

[73] Assignee: Van den Bergh Foods Co., Division of Conopco, Inc., Lisle, Ill.

[21] Appl. No.: 08/905,281

[22] Filed: Aug. 1, 1997

Related U.S. Application Data

[63] Continuation of application No. 08/511,429, Aug. 4, 1995, abandoned.

[51] Int. Cl.$^6$ ........................................................ A23B 4/22
[52] U.S. Cl. .............................. 426/52; 426/50; 426/518; 426/521; 426/615
[58] Field of Search ............................... 426/50, 615, 52, 426/518, 521

[56] References Cited

U.S. PATENT DOCUMENTS

| | | | |
|---|---|---|---|
| 2,534,263 | 12/1950 | Hills | 426/50 |
| 3,138,464 | 6/1964 | Kruse . | |
| 3,326,698 | 6/1967 | Sakamoto . | |
| 3,549,384 | 12/1970 | Walker et al. . | |
| 3,615,721 | 10/1971 | Silberman | 426/50 |
| 3,873,753 | 3/1975 | Nelson et al. . | |
| 4,194,016 | 3/1980 | Weaver et al. . | |
| 4,437,934 | 3/1984 | Nelson et al. . | |
| 4,547,375 | 10/1985 | Mersfelder et al. . | |
| 5,206,047 | 4/1993 | Crandall et al. . | |

OTHER PUBLICATIONS

McColloch et al., "Recent Developments of Practical Significance in the Field of Pectic Enzymes," Food Technology vol. 3, pp. 94–96 (1949).

McColloch et al., "Factors Influencing the Quality of Tomato Paste. II Pectic ChangesDuring Processing," Food Technology, vol. 4, pp. 339–343 (1950).

Sognefest et al., "Presterilization of Canned Tomato Juice," Food Technology, vol. 1, pp. 78–84 (1947).

Fennema, ed., "Principals of Food Science Part I–Food Chemistry," Marcel Deckker,Inc., New York, NY, pp. 117–119, 482 (1976).

Sellam et al., "The Role of Pectolytic and Cellulolytic Enzymes and Pathogenesis by Pathogens Involved in Storage Diseases of Onions," Egyptian Journal of Phytopathology, vol. 9, pp. 35–42 (1977).

Van Buren, "Improved Firmness Without Additives," Food Engineering, vol. 45, No. 5,p. 127 (1973).

Sistrunk et al., "Chemical and Physical Changes in Green Beans During Preparation and Processing," Food Technology, vol. 14, pp. 357–362 (1960).

Hills et al., "Enzyme–Demethylated Pectinates and Their Gelation," Food Technology, vol. 3, pp. 90–94 (1949).

Guild, "Tomato Production, Processing and Quality Evaluation," AVI Publishing Co. Inc., Westport, CT, pp. 151–162, 352, 362–363 (1974).

Priestly, "Effects of Heating of Foodstuffs," Applied Science Publishers Ltd., London,England, pp. 291–301, 329–331 (1979).

*Primary Examiner*—Helen Pratt
*Attorney, Agent, or Firm*—Gerard J. McGowan, Jr.

[57] ABSTRACT

A process for preparing fresh tomato sauce and the sauce prepared thereby. The sauce has a fresh taste and has good viscosity even though diced tomatoes provided therein are not subjected to an enzyme deactivation heating step. In the process, diced tomatoes and a tomato puree are combined in a kettle including firming salts, water and pectinase.

16 Claims, No Drawings

PROCESS FOR PREPARING A TOMATO SAUCE USING A PECTINASE ENZYME

This is a continuation application of Ser. No. 08/511,429, filed Aug. 4, 1995 now abandoned.

BACKGROUND OF THE INVENTION

Tomatoes have recently received attention as a healthful food, particularly in view of the carotenoids which they contain. Popular sources of tomatoes in the diet are spaghetti and other red pasta sauces. Many consumers prefer tomato sauces which are freshly prepared because of improved taste. However, a difficulty encountered in the commercial preparation of fresh sauces is that breaking or cutting of tomatoes, eg, during dicing or crushing, especially breaking or cutting the tomato skins, causes the release of enzymes which can result in a rapid and usually undesirable decrease in the viscosity of the product. Consequently, heating to elevated temperatures is used to deactivate these enzymes, with the resulting loss of taste found in processed, as opposed to fresh packed, sauces.

Using fresh tomato products in preparing a tomato sauce (particularly calcium-treated raw diced tomatoes) can result in the sauce gelling. This is a result of the pectin and pectin-related enzymes not being deactivated in the raw tomatoes by heat. Pectin exudes from the raw tomatoes and combines with the available calcium to form a calcium pectate gel. It is usual in the practice of making a spaghetti sauce to use canned or aseptically processed diced tomatoes. The heat processing of the diced tomatoes inactivates the pectin enzymes and sets the pectin in the diced tomatoes. But again, heat processing generally has an impact on taste.

Generally, the best diced tomatoes are made using calcium chloride to firm the dices prior to processing. The calcium treated diced tomatoes can be a source of calcium for the gelling formation, although most tomato products contain enough calcium for gel formation to occur even without an additional source of calcium. The source of pectin is the unprocessed diced tomatoes. Pectin can also come from any fresh puree used in making the sauce although the main source of the excess pectin related to the gel has been identified as coming from the raw diced tomatoes.

Two enzymes which have been implicated in the above are pectin methyl esterase, which catalyzes cleavage of methoxy groups from pectin, and pectinase (also known as polygalacturonase or PG) which catalyzes depolymerization of the cleaved pectin molecules, which causes the reduction in viscosity. It is the demethoxylated pectins which are most suseptible to forming gels by combining with calcium ions.

Pectinase is sometimes used to degrade soluble and insoluble pectins with varying degrees of esterification for viscosity reduction, clarification, and depectinization and maceration of plant tissue in the production of fruit and vegetable juices. It is known that pectin will be deactivated by depolymerization by a small amount of pectinase.

It is documented that raw garlic and onion will under specified process conditions cause a tomato product (i.e., a sauce) to gel. U.S. Pat. No. 4,547,375, to Mersfelder et al. addresses how to prevent these gels and/or use these types of gels to thicken tomato based products. Mersfelder et al. disclose using the gelation mechanism provided by releasing methyl pectin esterase from onion and garlic to demethoxylate the pectin available in the tomato based product to generate a supply of low methoxyl pectin to increase the viscosity of the sauce. They also disclose that in sauces wherein the tomatoes were initially heat treated to inactivate the enzymes, gelling can be prevented by, e.g., a) heating the onion or garlic prior to their addition to the sauce or b) the addition of pectinase. Crandal et al. U.S. Pat. No. 5,206,047 recognized that high rapid heat treatment of pectin-containing juices will prevent gelling. Crandal et al. were confronted with the fact that the product they wanted to make could not tolerate a high heat manufacturing process without losing its product benefit. Their solution was to subject their product to high shear to destroy or prevent the gel. Unfortunately, high shear tends to destroy the appearance of distinct diced tomatoes in a sauce. Moreover, to subject a fresh pack tomato based sauce to sufficient heat in a short enough time to prevent some of the gelation would produce a product that lacked the flavor and texture benefits derived from making the product at lower temperatures, but results in the product having an undesirable texture because of the gel.

SUMMARY OF THE INVENTION

The present inventors have found that even when fresh garlic and onion have been treated to prevent the release of pectin methyl pecterase and thereby prevent them from causing gelling in the tomato products, gels still occur in the fresh pack spaghetti sauces containing previously non-heat processed raw diced tomatoes. Raw diced tomatoes treated with calcium chloride to insure their firmness during the sauce processing are particularly susceptible to such gelling. The invention is directed to a process for producing a fresh pack tomato based sauce, preferably with portions of raw diced tomatoes, fresh garlic and fresh onion, and having a fresh taste and a desirable viscosity without the undesirable gelling.

In accordance with the invention, a fresh pack tomato sauce is made using cut or broken tomatoes, eg tomato dices, pieces, purees or pastes, by adding the broken tomatoes to a vessel and also, either before or after the addition of the broken tomatoes, adding pectinase. Preferably, the broken tomatoes are in the form of raw diced tomatoes (with or without added calcium for firming). Desirably, fresh onion, and fresh garlic are also added. The broken tomatoes, eg raw diced tomatoes, and preferably also the fresh onion and garlic, are added without gelling by adding a pectinase enzyme to the vessel prior to adding the diced tomatoes, fresh garlic, and fresh onion. At least a portion of the broken tomatoes is not heat treated to deactivate pectin-related enzymes. Preferably, substantially none of the diced tomatoes are heat treated to deactivate pectin-related enzymes.

The preferred method of enzyme addition is to add the pectinase to water and the optional calcium salt such as calcium chloride in the kettle, then to add the raw tomatoes for a short period of time (usually 1 to 5 minutes) and then to add a puree of fresh tomatoes and the rest of the sauce ingredients. The sauce can be held for periods of half to one hour, preferably at about 110° F. without causing an undesirable gel to form in the finished sauce or a loss of viscosity. The effective amount of the enzyme ranges from 0.01% to about 1% of the total weight of the sauce.

It is desirable that the addition of pectinase to the sauce be effected under controlled conditions. It has unexpectedly been found that the gel was completely and consistently eliminated in the fresh pack tomato sauce with added raw diced tomatoes, fresh garlic, and fresh onion, yet the viscosity of the sauce was good. This finding was especially surprising in view of the fact that pectinase is used to decrease viscosity and is implicated in the decrease in viscosity which often results naturally once a tomato has been cut if the product is not soon heated to a high enough temperature to deactivate the enzyme. Thus, use of pectinase according to the invention permits the sauce to have a fresh taste by rendering unnecessary the usual enzyme-deactivation (and taste impairing) heat treatment, while at the same time permitting the sauce to maintain a desirable viscosity and texture. Although sterilization prior to packing is usually necessary, heat processing can be kept to a minimum in making the sauce commercially sterile.

It was surprising that one could add pectinase to a sauce that was depending on the properties of pectin for its viscosity since it was expected that adding a pectinase to the sauce would adversely affect the viscosity of the sauce. While not wanting to be bound by theory, it is believed that the use of pectinase in the present invention limits the pectin/calcium interaction so that the original viscosity of the puree is maintained, but the pectin being added to the sauce by the raw tomatoes does not gel. The pectinase is not being used to destroy the tomato tissue of the diced tomatoes. Thus, pectinase is being used in conjunction with a low heat process to stabilize tomato sauce viscosity and tomato dice integrity instead of its common use to destroy either viscosity and/or plant tissue. The sauce is aseptically processed and is packed in glass or cans and is shelf stable at room temperature for extended periods of time.

If desired, mixtures of enzymes may be used including, In addition to pectinase, enzymes such as cellulase or hemicellulase.

For purposes of the invention, heat deactivation of pectin enzymes is considered to occur at temperatures of 180° F. or more.

In order to preserve the fresh taste of the product, it is especially preferred that no tomato ingredients be used which have been previously heated, ie, heated outside of the immediate sauce preparation procedure.

For a more complete understanding of the above and other features and advantages of the invention, reference should be made to the following detailed description of preferred embodiments and to the accompanying drawings.

DETAILED DESCRIPTION OF THE INVENTION

The tomatoes used in the invention are preferably freshly picked.

Pectinase, also known as PG or polygalacturonase, is available under the brand name Pectinase AT from Solvay Enzymes of Elkhart, Ind. Pectinase AT has an activity of 150,000 ADJU/gram. ADJU's are apple depectinase juice units. Another enzyme which may be used is sold as Clarex L, also by Solvay, and has an activity of 15,000 ADJU/ml. Clarex ML is a pectinase having a pectinase activity of 40,000 ADJU, which also contains hemicellulase and cellulase enzymes. The Clarex ML product should be used in the present invention at approximately four times the amount of the Pectinase AT enzyme. The activities ratio of pectinase to cellulase in the Clarex ML product is 10:1 whereas the activities ratio of pectinase to hemicellulase in the Clarex ML product is 1:4. The ratio of activities for hemicellulase to cellulase in Clarex ML is 40:1. The pectinase activity in the enzyme preparation may, for example be within the range of from 35,000 to 150,000 ADJU/gram. from eg Pectinase may be obtained from Quest, International as Biopectinase. Pectinase may also be obtained from Novo Nordisk of New York, N.Y.

The pectinase may be fungal or from plants such as tomatoes and other fruits or vegetables. Fungal pectinase is preferred. Pectinase is used at a level of from 0.005 to 0.2 weight percent of the final sauce. The amount of pectinase used may be adjusted based on the ambient temperature which the tomatoes experience prior to dicing since higher temperatures can increase pectinase activity.

If it is desired to use a freshly prepared tomato puree in preparing the sauce, in addition to diced or other broken tomatoes, it may be desirable to heat the puree prior to addition to the vessel. If desired, this may be conducted at temperatures high enough to deactivate enzymes, without departing from the present invention since the diced tomatoes will still contain active enzymes which induce the problematic gel formation to which the present invention provides a solution.

Preferably at least 10 wt % (based on the weight of the final sauce product) and more preferably from 20–45 wt. % of tomatoes in the sauce are subjected to temperatures which do not exceed 180° F., preferably 170° F., especially 150° F. prior to sterilization. Commercial sterilization is desirably carried out by heating at between 195 and 200° F. for about 10–20 minutes. For instance, the sauce can be heated at 195° F. for 10 minutes, at 200° F. for 5 minutes or at 185° F. for 15 minutes. Desirably, the exposure of the sauce to high temperatures is minimized to preserve the fresh taste.

The amount of diced tomato preferably ranges from 10 to 40 wt % based on the weight of the final sauce. Tomato puree may be used at from 5 to 45 wt % basis final sauce, e.g., 30–45 wt. %. Water will typically be added at from 10–45 wt %.

Spaghetti sauces often include one or more vegetable oils. Typical examples of appropriate vegetable oils include corn oil, olive oil, canola oil and soybean oil, although almost any vegetable oil can be used. The oil may be used at from 0 to 15 wt. %, especially from 0.5 to 12 wt. %. and more narrowly from 2 to 9 wt. %. However, the sauce may also be free of added triglyceride oil or fat. If triglycerides are present it is preferred that they be in the form of vegetable oil rather than animal fat. Sauces prepared in accordance with the invention will desirably have a Bostwick viscosity of from 5 to 7 cm, especially from 5.5 to 6.5 cm, most preferably 6 cm.

The Bostwick viscosity may be determined as follows. The sauce is placed in a viscometer instrument called a Bostwick Consistometer. The Bostwick Consistometer must be at room temperature (25° C.) and be clean and dry. It must be leveled. A small carpenter's level works well. The puree or paste is diluted to 12 brix and mixed until there are no visible lumps of tomato puree and/or paste. The chamber is filled full. The excess material is scraped off of the top of the chamber with a straight edge. Release the gate and time for 30 seconds. Record the distance the tomato puree/paste has traveled in cm. The sauce will move to a distance corresponding to its viscosity; the higher the viscosity, the less distance the paste will move. The Bostwick number is obtained by measuring the distance as calibrated on the instrument. The soluble solids of the sauce will typically range from 10 to 16, preferably from 12 to 15 brix.

The pH of the sauce may be adjusted as desired using edible acids including citric, malic, lactic, acetic or gluconic acids. If necessary, the pH may be buffered using a buffer system such as citric acid/sodium citrate, gluconic acid/sodium gluconate, acetic acid/sodium acetate, or malic acid/sodium malate systems. The pH of the sauce of the invention may range from about 4 to about 6, especially from 4 to 5.

In addition to Alluvium vegetables such as onion and garlic, other ingredients which may be used in the sauce include table salt, sweeteners such as sucrose, pepper and garlic and onion powders. If desired, the Alluvium ingredients may be blanched, eg heated at a temperature of above 160 °F. prior to addition to the tomato ingredients of the product.

Seasonings and spices may include pepper, such as black pepper and red pepper, basil, dry basil, oregano, thyme, bell pepper, celery, bay leaf, fennel and parsley. Chopped vegetables, such as green and red peppers and carrots, and meats, such as ground beef, may be included, if desired.

The sauce of the invention is typically prepared by adding freshly diced tomatoes to a kettle to which has already been added water, firming salts and pectinase. Desirably, the diced tomatoes are treated as early as possible in the process with the firming salts. A fresh puree which has a soluble solids content of about 20 brix is then added. The puree is preferably at 20 brix, eg from 15 to 25 brix rather than the more typical 32 brix, so as to be subjected to less heat during the evaporation process. However, 31 or 32 brix paste could also be used. The puree will preferably have been subjected to a break temperature of approximately 200° F. for 5 to 10 minutes. The sauce is held for an hour at from room temperature up to 110° F. or another appropriate temperature after which the sauce is sterilized and packed. Preferably, the sauce is subjected to commercial sterilization conditions which are less severe, to enhance fresh taste.

The order of addition of ingredients may be varied, so long as the viscosity is not undesirably diminished. For instance, the diced tomatoes can be added to the firming salt and water and mixed, after which pectinase can be added and mixed, after which the puree, spices and remainder of ingredients can be added. Alternatively, the pectinase can be added immediately after the puree.

The diced tomatoes are exposed to firming salts to preserve their viscosity. Calcium chloride is a preferred firming salt. Another preferred firming salt is calcium citrate. Others include mono calcium phosphate and calcium lactate. Calcium chloride is used in an amount not to exceed 0.222 wt % of the sauce, preferably from 0.095 wt % to 0.222 wt %.

To ascertain whether a sauce is to be considered gelled, i.e., to possess an undesirable gel, gel strength assessment is determined by a visual analysis of the cooled product in a jar. A gelled product retains the shape of the jar and pulls away cleanly from the side of the jar when tipped or rotated. The product surfaces appear shiny on gelled products. A non-gelled product appears uniformly pulpy and not shiny.

A visual assessment of the jarred product is made individually by one or more, preferably more than one, especially four, people familiar with identifying gelling in tomato based products. The scale used is a six point scale adopted from gel assessments made by Crandal et al. in U.S. Pat. No. 5,206,047. They refer to a Gel Evaluation test by Redd et. al."Quality Control Manual for Citrus Processing Plants." (1986 Intercit, Inc.). The Crandal et al. and Redd et al. references are incorporated herein by reference.

The scale is as follows:
0=Product of uniform appearance, contains no gel lumps.
1=Product with a few small gel lumps but no tendency to mound.
2=Product contains some gelled lumps with a slight tendency to mound.
3=Product has a definite degree of gelation with a slight tendency to mound but does not retain the shape of the container.
4=Product is over 75% gelled with a definite retention of the shape of the container.
5=Product is 100% gelled with the product retaining the fine detailed shape of the container.

Products with a gel score above 3 are not considered gelled. Products with a score of 3 are considered borderline and could be rejected from a quality point of view as having an objectionable amount of gel. The amount of gel expected ranges in the 2 or below category. While scores of 3 might be accepted, adjustments in the amount of enzyme would be considered.

EXAMPLE 1

Example 1 illustrates the preferred method of gel prevention in the production of fresh pack tomato sauces processed at optimum temperatures to retain the sauce freshness without compromising the product stability or safety.

A tomato sauce product is prepared according to the following formula:

| Ingredient | Wt. by % |
|---|---|
| Water | 29.05 |
| Fresh Tomato Puree | 30.00 |
| Raw Diced Tomatoes | 30.00 |
| Sweetener | 6.00 |
| Fresh Onions | 1.00 |
| Fresh Garlic | .50 |
| Pectinase* | .05 |
| Other Seasonings and Minor Ingredients | 3.40 |
| Total | 100.0 |

*Varies from .005 to .20 depending on the raw tomatoes.
*The actual amount of the pectinase is also dependent on the activity of the enzyme.

The fresh raw tomatoes are diced and conveyed immediately to a kettle waiting with the pectinase, firming salts, and water. The mixture is allowed to mix at ambient temperature for a minimum of 5 to 10 minutes. Fresh onions and garlic are optionally sauteed (i.e. blanched) and added to the mixture. The fresh tomato puree is pumped from the concentrator to the kettle and the remaining fresh ingredients (basil), seasonings and other minor ingredients are added. To preserve freshness the sauce is held at 110° F. for up to an hour. The batch is immediately heated via a heat exchanger to 195° F., filled into the jars and held for the minimum time (about ten minutes). Once the product has been exposed to at least minimum commercial sterilization conditions, it is immediately cooled to ambient temperature.

When this process is followed without the use of the pectinase or a pectinase-containing enzyme mix, the sauce gels on cooling. The sauces made with from 10 to 40 percent raw tomatoes do not gel when the pectinase or pectinase containing enzyme is used in this process.

Instead of holding the batch at 110° F., it may be held at room temperature or up to 110° F. or from 150 to 175° F. for up to an hour. The lower temperatures are preferred.

EXAMPLE 2

Example 1 illustrates the preferred method of gel prevention in the production of fresh pack tomato sauces processed at optimum temperatures to retain the sauce freshness without compromising the product stability or safety. However, a part of the discovery of the invention is that an enzyme mixture containing a combination of pectinase, cellulase and hemicellulase is effective in preventing the gelation of fresh pack tomato sauces.

A tomato sauce product is prepared according to the following formula:

| Ingredient | Wt. by % |
| --- | --- |
| Water | 29.05 |
| Fresh Tomato Puree | 30.00 |
| Raw Diced Tomatoes | 30.00 |
| Sweetener | 6.00 |
| Fresh Onions | 1.00 |
| Fresh Garlic | .50 |
| Enzyme Mix* (Pectinase, Cellulase and Hemicellulase) | .20 |
| Other Seasonings and Minor Ingredients | 3.40 |
| Total | 100.00 |

*Varies from .005 to .20 depending on the raw tomatoes.
*The actual amount of the pectinase blend is also dependent on the activity of the enzyme.

The fresh raw tomatoes are diced and conveyed immediately to a kettle waiting with the enzyme mix (pectinase, cellulase and hemicellulase), calcium chloride and water. The, mixture is allowed to mix at ambient temperature for a minimum of 5 to 10 minutes. Fresh onions and garlic which are optionally sauteed (i..e. blanched) are added to the mixture. The fresh tomato puree is pumped from the concentrator to the kettle and the remaining fresh ingredients (basil), seasonings, and other minor ingredients are added, To preserve freshness the sauce is held at room temperature for up to an hour. The batch is immediately heated via a heat exchanger to 195° F., filled into 24 oz. jars and held for the minimum time (about ten minutes). Once the product has been exposed to the commercial sterilization conditions, it is immediately cooled to ambient temperature.

When this fresh pack process is followed without the use of the pectinase or a pectinase containing enzyme, the sauce gels on cooling. Sauces made with from 10 to 40 percent raw tomatoes do not gel when the pectinase or pectinase-containing enzyme mix are used in this process.

The inventors have found that not all gels of tomato sauces are pectin gels. Particularly when processed tomatoes are used in making the tomato sauce, cellulose gels were found. These were confirmed by dissolving the gels with cellulose. Therefore it was felt that some cellulase would be useful in controlling the tomato sauce gel. However, we have found that the gel from pectin was on such a larger scale than gels from cellulose that the pectinase become the preferred enzyme of choice.

EXAMPLE 3

The procedure of Example 1 is followed, except that the dice amounts and enzyme amounts are varied as set forth below. Bostwick viscosity values are measured for the various sauces, as set forth below.

| Example | Dice Amount | Enzyme wt. % | Sauce Bostwick |
| --- | --- | --- | --- |
| A | 11.4 | 0.005–0.10 | 6.1 |
| B | 13.2 | 0.010–0.030 | 5.5 |
| C | 16.0 | 0.010–0.030 | 5.5 |
| D | 32.7 | 0.011–0.100 | 5.6 |
| E | 12 | 0.000 | GEL |

The presence of a gel is determined by four people familiar with the detection of gels in tomato products using the procedure set forth above.

EXAMPLE 4

Sensory data for a fresh pack sauce prepared according to Example 1 is compared with that for commercially available, remanufactured, tomato-based sauce made by heating substantially all of the cut tomatoes shortly after they have been picked and without addition of pectinase. The remanufactured product is a fresh pack formula made with heat treated tomato dices and 31 brix paste. The results are as follows:

| Product | Color | Consistency | Chunky Appearance | No. of Tomato Pieces | Processed Tomato Flavor |
| --- | --- | --- | --- | --- | --- |
| Fresh | 4 | 4 | 6 | 5 | 3.3 |
| Remanfctd | 4 | 4.5 | 4 | 3.5 | 4.5 |

Key:
Color: 1 = orange 5 = red 9 = brown
Consistency: 1 = very thin 9 = very thick
Chunky: 1 = smooth looking 9 = chunky looking
Amount of Tomato pieces: 1 = very few 9 = very chunky
Both formulas started with the same amount of tomatoes
Processed Flavor: 1 = Fresh 5 = Processed 9 = Overcooked The fresh pack sauce is fresher than the remanufactured product. The fresh pack sauce retains more tomato piece integrity. The remanufactures sauce has an insignificant amount of higher consistency.

It will be noted that the enzyme mixture requires about 4 times more enzyme than the straight pectinase. The reason for this is that the source of the pectinase enzyme may have a much higher activity level than the mixed enzyme.

The firming agent mentioned relies on the calcium in it to interact with the raw diced tomatoes to give them firmness. This same calcium will combine with the low methoxy pectin in the tomato sauce to form very tight gels. The pectinase then becomes key to having firm tomatoes with a non gelled viscous sauce.

It should be understood, of course, that the specific forms of the invention herein illustrated and described are intended to be representative only, as certain changes may be made therein without departing from the clear teaching of the disclosure. Accordingly, reference should be made to the following appended claims in determining the full scope of the invention.

What is claimed is:

1. A process for preparing a tomato product comprising
   a) adding broken tomatoes which have not been subject to a pectin enzyme heat deactivation step to a vessel,
   b) before or after step a), adding pectinase to the vessel,
   c) subsequently, sterilizing said broken tomatoes.

2. The process according to claim 1 further comprising adding further broken tomatoes in the form of a tomato puree to said vessel before or after step a).

3. The process according to claim 2 further comprising adding Allium ingredients to the vessel before or after step a).

4. The process according to claim 1 wherein water is added to said vessel before or after step a).

5. The process according to claim 1 wherein pectinase is added to the vessel before step a).

6. The process according to claim 1 wherein firming salts are added to the vessel.

7. The process according to claim 6 wherein the firming salts are added to the vessel before the broken tomatoes are added.

8. The process according to claim 6 wherein the firming salts include calcium salts.

9. The process according to claim 8 wherein the firming salts include calcium chloride.

10. The process according to claim 1 wherein broken tomatoes include diced tomatoes and the temperature to which the diced tomatoes are exposed does not exceed 155° F. prior to sterilization.

11. The process according to claim 10 wherein the temperatures to which the diced tomatoes are exposed do not exceed 110° F. prior to sterilization.

12. The process according to claim 1 wherein the pectinase is added at from 0.005 to 0.20 wt. % of the final tomato product.

13. The process according to claim 1 comprising diced tomatoes in the tomato product.

14. The process according to claim 13 wherein the diced tomatoes are added in an amount of from 10 to 40 wt. % of the tomato product.

15. The process according to claim 1 wherein before or after step a) cellulase is added to the vessel.

16. The process according to claim 1 wherein before or after step a) hemicellulase is added to the vessel.

* * * * *